(12) United States Patent
Sidebotham (10) Patent No.: US 7,547,328 B2
(45) Date of Patent: Jun. 16, 2009

(54) CANINE FEMORAL STEM SYSTEM (76) Inventor: Christopher G. Sidebotham, 27 Kings Brook Ct., Mendham, NJ (US) 07945

( * ) Notice: Subject to any disclaimer, the term of this patent is extended or adjusted under 35 U.S.C. 154(b) by 280 days.

(21) Appl. No.: 10/853,971

(22) Filed: May 26, 2004

(65) Prior Publication Data

US 2005/0267586 A1 Dec. 1, 2005

(51) Int. Cl.
A61F 2/36 (2006.01)
(52) U.S. Cl. .................................. 623/23.26
(58) Field of Classification Search ...... 623/22.4–23.38
See application file for complete search history.

(56) References Cited

U.S. PATENT DOCUMENTS

| | | | | |
|---|---|---|---|---|
| 4,031,571 | A | | 6/1977 | Heimke et al. ............... 3/1.913 |
| 4,407,022 | A | | 10/1983 | Heimke et al. ............... 3/1.913 |
| 4,546,501 | A | | 10/1985 | Gustilo et al. .................. 623/23 |
| 4,550,448 | A | * | 11/1985 | Kenna ......................... 623/23.6 |
| 4,589,883 | A | | 5/1986 | Kenna .......................... 623/22 |
| 4,612,160 | A | * | 9/1986 | Donlevy et al. ................ 419/2 |
| 4,718,912 | A | | 1/1988 | Crowninshield ............. 623/23 |
| 5,019,108 | A | * | 5/1991 | Bertin et al. ............. 623/23.28 |
| 5,027,998 | A | * | 7/1991 | Bugle ........................ 228/44.5 |
| 5,047,056 | A | * | 9/1991 | Kenna ........................ 623/23.44 |
| 5,047,062 | A | | 9/1991 | Pappas et al. ................. 623/23 |
| 5,108,452 | A | | 4/1992 | Fallin .......................... 623/23 |
| 5,116,379 | A | | 5/1992 | McLardy-Smith ........... 623/23 |
| 5,156,627 | A | * | 10/1992 | Amstutz et al. .......... 623/22.41 |
| 5,176,712 | A | * | 1/1993 | Homsy .................... 623/23.36 |
| 5,201,766 | A | * | 4/1993 | Georgette ................... 128/898 |
| 5,286,260 | A | * | 2/1994 | Bolesky et al. ........... 623/22.42 |
| 5,336,265 | A | | 8/1994 | Serbousek et al. ............. 623/18 |
| 5,387,243 | A | * | 2/1995 | Devanathan ................. 128/898 |
| 5,456,717 | A | | 10/1995 | Zweymüller et al. ........... 623/8 |
| 5,507,833 | A | | 4/1996 | Bohn .......................... 623/23 |
| 5,725,594 | A | | 3/1998 | McTighe et al. .............. 623/23 |
| 5,725,595 | A | | 3/1998 | Gustilo ........................ 623/23 |
| 5,755,805 | A | | 5/1998 | Whiteside .................... 623/22 |
| 5,871,549 | A | | 2/1999 | Jayashankar et al. .......... 623/22 |
| 6,102,957 | A | | 8/2000 | Noble et al. .................. 623/23 |
| 6,193,761 | B1 | * | 2/2001 | Treacy .................... 623/23.55 |
| 6,200,349 | B1 | * | 3/2001 | Naybour .................. 623/23.15 |
| 6,221,110 | B1 | * | 4/2001 | Copf ....................... 623/22.21 |
| 6,413,280 | B1 | | 7/2002 | Feiler ....................... 623/22.15 |
| 6,428,578 | B2 | | 8/2002 | White ...................... 623/23.22 |

(Continued)

Primary Examiner—Corrine McDermott
Assistant Examiner—Cheryl Miller
(74) Attorney, Agent, or Firm—Ernest D. Buff & Associates, LLC; Ernest D. Buff; Harry Anagnostopoulos (57) ABSTRACT A canine femoral stem system provides a set of sizes of stems designed to fit in a reamed femoral bone canal with controlled interference. The canine femoral stems can be implanted using either a cemented or cementless procedures. Cementless stems have a porous coating of sintered beads on the tapered proximal section providing interference with reamed femoral canal causing friction and initial stability. The distal end of the stem has a tapered fit and contacts the lower region of the reamed femoral bone canal due to curvature of the stem providing distal stability. The porous coating encourages bone ingrowth in the cementless system or cement penetration resulting in long term stability. The cementless system uses either cast cobalt chromium stems with 250±50 μm beads of cobalt chromium or Ti- 6Al- 4V stem with 250±50 μm beads of chemically pure titanium.

5 Claims, 5 Drawing Sheets

U.S. PATENT DOCUMENTS

| | | | |
|---|---|---|---|
| 6,464,728 B1 | 10/2002 | Murray | 623/22.42 |
| 6,695,884 B1 * | 2/2004 | Townley | 623/23.26 |
| 6,974,483 B2 * | 12/2005 | Murray | 623/22.42 |
| 7,060,102 B2 * | 6/2006 | Thompson et al. | 623/23.35 |
| 2001/0008981 A1 * | 7/2001 | Masini | 623/22.42 |
| 2002/0058999 A1 | 5/2002 | Dwyer et al. | 623/22.42 |
| 2002/0138151 A1 | 9/2002 | Hubbard et al. | 623/22.43 |
| 2003/0074079 A1 | 4/2003 | McTighe et al. | 623/22.42 |
| 2004/0010319 A1 * | 1/2004 | McTighe et al. | 623/23.21 |
| 2004/0107001 A1 * | 6/2004 | Cheal et al. | 623/22.42 |
| 2005/0055103 A1 * | 3/2005 | Badatcheff et al. | 623/22.42 |
| 2006/0041317 A1 * | 2/2006 | Hazebrouck et al. | 623/23.39 |

\* cited by examiner

CANINE FEMORAL STEM SYSTEM

BACKGROUND OF THE INVENTION

1. Field of the Invention

The present invention relates to a canine femoral stem for canine hip replacements; and more particularly to a femoral stem construction that achieves a firm bond between the femoral stem and the underlying reamed bone canal, thereby providing initial stability immediately following surgery, together with long-term stability.

2. Description of the Prior Art

Many patents address issues related to hip replacement, and especially to femoral stem replacement. These patents disclose methods to attach the femoral stem into a reamed bone cavity using cements having various formulations, or screws and barbs associated with cementless procedures. Several patents address primarily human hip replacement while a few of them relate to canine hip replacement. There are large significant differences between a femoral stem designed for human hip replacement and one appointed for canine hip replacement. These differences are in part due to the larger overall weight of the human body as compared to that of a dog. Human devices require femoral stems having larger diameter and lengths, and additional attachments heretofore considered unnecessary for canine use. These dimensions are severely restricted when femoral stems are used in canines. The design of femoral stem must provide initial stability immediately after surgery and restrict the movement of the implanted femoral stem so as to extend the in-service life of the attachment between the femoral stem and the bone canal. Thus, the geometries of femoral stems appointed for canine use are required to be different from those used in humans.

U.S. Pat. No. 4,031,571 to Heimke et al. discloses a hip endoprosthesis having stepped load-transferring surfaces. The thigh portion of an endoprosthesis for hip joints is provided with stepped projecting surfaces to distribute forces in the bone tissue. Projecting surfaces provide a larger area of contact with the bone tissue, reducing stress intensity. These steps of projections are provided at opposing angles in the proximal end to provide initial stability of insertion of the animal's femoral stem. The projections are larger in size and insertion of the implant into bone cavity results in gaps between the implant and the bone, contrary to what is shown in the figure. This lack of contact between the steps will prevent bone filling and does not provide increased contact area as claimed in the patent. Due to the large size of these projections, this device is obviously intended for human use; and would not be suitable for use in canines.

U.S. Pat. No. 4,407,022 to Heimke et al. discloses a femur component for an artificial hip joint. Initial stability of the animal femoral stem is achieved by use of steps that are inclined to the longitudinal axis of the femoral implant step. One set of steps faces upward and a second set faces downwards. Fitting this stepped stem into a bone cavity pushes the larger size into the bone cavity creating a larger hole. This prevents bone contact with the portions of the implant that do not carry the stepped regions, creating a poor bond between the femoral stem and the bone. Also, the surface of the femoral stem is not coated with a porous coating for bone ingrowth. Rather, the device disclosed by the '022 patent relies on the steps to provide initial and long term implant stability. Due to the large size of these projections, this device is clearly intended for human use; it would not be suitable for use in canines.

U.S. Pat. No. 4,546,501 to Gustilo et al discloses a hip prosthesis. A femoral insert combines bone ingrowth surfaces in the proximal portion of the shaft, which is wide in the medial-lateral direction and curved in the medial aspect with a distal portion, which has a round cross-section and is curved in the direction of the anterior bow of the femur. Accordingly, firm fixation of the implant is initially provided by the distal portion functioning as an intramedullary rod, while long-term stabilization is achieved proximally through bone ingrowth. Also, the neck connecting the spherical head to the shaft through the collar is anteverted with respect to the collar at an angle of about 10 degrees to 12 degrees. The prosthesis for the left femur is basically a mirror image of the prosthesis for the right femur. The '501 patent discloses a hip prosthesis for humans based on the size of the femoral head, which is 28 mm. Initial stabilization is accomplished by a curved fit between the distal end of the femoral stem and the bone cavity. A collar resting on the bone's outer surface provides additional rigidity. There is no real support provided at the proximal end. A porous bone bonding coating is only provided on the sides of the rectangular cross section implant device; it does not completely surround the proximal region of the implant. The device disclosed by the '501 patent would not be suitable for canine use.

U.S. Pat. No. 4,589,883 to Kenna discloses a femoral hip prosthesis. A femoral hip prosthesis comprises a stem component generally divided into a proximal portion and a substantially longer distal portion. The stem has a slight posterior bow along its length. The proximal portion includes a slight twist of from about 5 degrees to 15 degrees. The twist extends in a direction from the anterior to the posterior face of the stem through the medial face thereof. Stem characteristics provide a glove fit when the device is inserted into a prepared intermedullary canal in the femur. A curvature in the mid portion of the femoral stem binds the implant against the bone cavity, providing initial stability. No support is provided elsewhere. The proximal portion of the femoral stem is coated with bone ingrowth coating. Owing to the large angle of twist (i.e. 5-15 degrees), the femoral stem disclosed by the '883 patent is appointed for use in humans; but not canines.

U.S. Pat. No. 4,718,912 to Crowninshield discloses a femoral component and method of constructing the same. A femoral component for a hip prosthesis includes a stem with a porous surface or the like to enhance bone fixation. The porous surface is applied to the stem in a predetermined manner to accommodate stress lines for the stem and generate a curvilinear inferior boundary for the porous surface. It uses a porous coating that encourages bone ingrowth at locations where stress is low, accommodating the differences in stress experienced by the anterior side as compared to the posterior side of the stem. The femoral implant device is said to be useful in human; its suitability for canine use is not disclosed. There is no provision for providing initial stability of the femoral stem, since stability is based on bone ingrowth in the porous region, which is a long-term stability issue.

U.S. Pat. No. 5,047,056 to Kenna discloses a canine hip prosthesis with a porous coating for bone ingrowth. The stem for insertion into the intramedullary canal of a canine femur is divided into a proximal portion and a longer distal portion. A compound curvature along its length provides a glove-like fit in the prepared intramedullary canal of the canine femur. The proximal portion of the stem includes a porous coating of two layers of ball-shaped metallic particles bonded together at their points of contact. Pore size of the coating ranges from about 0.014 to 0.020 inches. The stem of the canine hip prosthesis is held in place in the bone cavity primarily by the posterior bow. Further curvature in the proximal portion and the overall three dimensional curvature create a glove-like fit. The initial stability is entirely provided by this curvature. No support is provided either at the distal or proximal end. This curvature does not result in intimate contact with the bone cavity. Porous coating applied at the proximal end and bone ingrowth is hindered due to micro motions at this proximal end.

U.S. Pat. No. 5,047,062 to Pappas et al discloses a femoral stem-type prosthesis. The bending stress in the neck of the femoral stem is reduced by limiting the length of the neck and positioning the femoral head nearly in line with the right edge of the collar. There is no disclosure on how the stem is attached or how initial stability is attained. Neither is there any disclosure in the patent that the femoral stem could be used for canine applications.

U.S. Pat. No. 5,108,452 to Fallin discloses a modular hip prosthesis. A modular hip prosthesis can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas. A stem section of the prosthesis has a generally rounded cross-sectional area. The stem is tapered to receive a tubular extension sleeve with a hollowed portion corresponding in shape to the stem portion of the prosthesis. The tubular extension sleeve has an open-end portion receptive of the lower tapering stem of the prosthesis body. The stem portion includes an internal bore. An attachment in the form of an elongated screw is provided for connection to the stem internal bore. By this means the extension sleeve and the prosthesis body are secured together, forming a compressive sealed connection therebetween. The modular hip prosthesis is appointed for human use, not canine use. It employs a number of femoral stem components that work collectively to form an integral custom shaped femoral stem. The stem itself is made in several pieces. A single bolt, when tightened, bends the cylindrical distal end at a slight angle complying with the bone cavity. The presence of bolts in the system holding together a geometry subjected to loading creates problems. Motion of the bolt and components of the device, or slight deformation of the bone cavity due to load, causes shifting of the device. There is no porous coating for bone attachment. The cylindrical distal end does not provide firm attachment. Moreover, in the device disclosed by the '452 patent, placement of the implant relies on the overall bending of the cylindrical extension. The initial and long-term stability of this patented device is therefore questionable. Various femoral heads are provided; but they are attached through a collar providing long-term reliability problems. The device taught by the '452 patent is not suitable for canine use.

U.S. Pat. No. 5,116,379 to McLardy-Smith discloses a prosthesis. A hole in the proximal section and the shaft of the prosthesis has a diameter over 12 mm. As such, the prosthesis disclosed by the patent is intended strictly for human use. The distal section and proximal section are separately formed and held together by the shaft. Generally, the proximal section is wedge fitted into the bone cavity. Alternatively, a smaller proximal section may be cemented within the bone cavity. There always exists a play between the shaft and the hole, so that the proximal section may be slid over the shaft. This very play causes initial and long-term instability problems. There is no coating to create bone ingrowth. The device disclosed by the '379 patent would not be suitable for canine use.

U.S. Pat. No. 5,336,265 to Serbousek et al. discloses a reduced stiffness femoral hip implant. A femoral component of an artificial hip joint includes an elongated stem with a single longitudinally extending, medially facing, groove in its outer surface intermediate its proximal and distal ends. The dimensions of the groove are chosen so as to obtain constant stiffness or, alternatively, a predetermined stiffness of the stem between the proximal and distal ends. In either event, the stem has a magnitude of stiffness no greater than that at which stress shielding of the first bone would occur. The groove and the outer surface of the stem intersect at an outer rim. The component is preferably composed of titanium, titanium alloy, or cobalt-chromium alloy. The outer surface of the stem may be provided with a porous medium for encouraging bone ingrowth fixation. This reduced stiffness femoral hip implant is said to be appointed for human use. There is no initial stability in this device. Long-term stability is provided by the bone ingrowth coating if the movement of the implant is restricted. However this restriction is not readily accomplished by the design of the reduced stiffness femoral hip implant. The device disclosed by the '265 patent would not be suitable for canine use.

U.S. Pat. No. 5,456,717 to Zweymuller et al. discloses a stem for a femoral hip-joint endoprosthesis. The stem for the femoral hip-joint endoprosthesis comprises a shaft, which is substantially rectangular in cross section, with a distal and a proximal end wherein the distal end tapers substantially conically and the proximal end (16) comprises an insertion means and an extraction means for the insertion and for the extraction of the stem into a narrow space within a femur. A cone is provided to receive a joint ball. The cone is connected to the proximal end of the shaft by way of a neck. The disclosure does not state that the femoral hip joint is for canine use. It would be very difficult to create a rectangular bone cavity in a dog to receive this rectangular stem femoral stem. In addition, there is no provision for initial stability or presence of a porous coating for long-term stability due to bone ingrowth.

U.S. Pat. No. 5,507,833 to Bohn discloses a hip replacement system and method for implanting the same. A femoral stem has a series of dimples provided at the distal and proximal ends of the femoral stem, which may be coated with hydroxyapatite to create bone bonding. This is a device for human use based on the length of the femur stem (approximately 100 mm to 180 mm). There is no initial stability since both distal and proximal ends of the femoral stem await bone growth.

U.S. Pat. No. 5,725,594 to McTighe et al. discloses a proximal conical stem. A cementless femoral hip stem component includes an elongate stem having opposing distal and proximal sections. The proximal section includes a conical stem surface, which terminates in a proximal end. A collar having a conical undersurface extends laterally outward from the proximal end of the stem. The proximal conical stem portion and the conical undersurface of the collar cooperatively define a unitary double-cone contact surface to allow the collar to subsidably engage with external cortical bone in tandem with the proximal conical stem subsidably engaging with the internal femoral canal. The proximal portion of the femoral stem is made up of two opposing conical and frusto-conical sections, thereby making contact with their corresponding bones to provide improved load capacity and improved bone ingrowth. This is a device made for human use; no disclosure is contained by the patent concerning canine use.

U.S. Pat. No. 5,725,595 to Gustilo discloses a cannulated cementless hip stem prosthesis. A canulae feature of the stem component permits the stem to be precisely aligned in an intramedullary canal which is prepared in a person. The distal end is flexible while the proximal end contains bone ingrowth stimulating bead coating. This is a device for human use and not for canine use.

U.S. Pat. No. 5,755,805 to Whiteside discloses a tapered prosthesis component to be used primarily in humans. The tapered prosthesis component is rectangular in shape with ridges and steps cut into the tapered portion to anchor the component into a bone cavity. The wedging action and cutting action of the ridges is set to anchor the component into the bone. If the tapered bone cavity is not prepared correctly, the femur bone may fracture. There is no porous coating on the implant to encourage bone growth. Producing this matching tapered bone cavity by reaming would be difficult in canines and thus is not suitable for canine use.

U.S. Pat. No. 5,871,549 to Jayashankar et al. discloses a femoral stem with reduced coefficient of friction with respect to bone cement. This cemented femoral stem has a lubricious coating between the femoral stem and the bone cement to reduce damage caused by bone cement and the creation of wear particles. The reduced coefficient of friction also allows movement of the femoral stem in the bone cavity with the bone cement, compromising the initial stability of the femur implant. This is not a femoral implant for canine use.

U.S. Pat. No. 6,102,957 to Noble et al. discloses an asymmetric hip stem for use in cementless hip replacement procedures. The stem comprises a proximal region having a novel three-dimensional configuration that allows for better fit and stability of the stem within the femoral intramedullary canal, with minimal removal of strong bone therefrom. The stem further includes a twist isolated in the mid-stem region to improve fit while minimizing enlargement of the femoral canal. A distal end has a rotated internal slot, which reduces bending stiffness of the stem in both the coronal and sagittal planes. This asymmetric hip stem is for human use. Its length is preferably about 4.5 inches to 6.5 inches (col. 5, lines 41-43). Its femoral neck is relatively long, being about 18 mm (col. 5, lines 13-17). Complex asymmetric geometry is used to improve fit and stress distribution. The device disclosed by the patent is not suitable for use in canines.

U.S. Pat. No. 6,413,280 to Feiler discloses hip joint prosthesis. The patent discloses hip joint prosthesis for humans which provides a larger degree of hyperflexion of the leg by designing a neck which has a complex shape. The acetabular cup is notched to prevent interference of the neck during hyperflexion. This femoral stem is not for canine use.

U.S. Pat. No. 6,428,578 to White discloses a modular prosthesis and connector therefor. Three components: a stem, a sleeve and a body, are assembled during surgery at the proper height to create the femoral stem. The body has a bore into which a sleeve and then the stem is inserted. Force is applied to lock the stem within the sleeve. A single unit meets different size needs. No disclosure is contained by the patent concerning a system for selection of differently sized femoral stems. Moreover the device disclosed by the patent is intended for use in humans, not for canine use.

U.S. Pat. No. 6,464,728 to Murray discloses a modular neck for femur replacement surgery. The modular neck is attached into a blind hole in the stem at selected anteversion to meet patient requirements. The device disclosed by the patent is designed for human use and is not for canine use.

U.S. patent application No. 2002/0058999 to Dwyer et al. discloses a modular prosthesis having a stem component with a counterbored cavity defined therein and an associated method. The modular prosthesis is disclosed as being suitable for human use; not for canine use. It uses a common and proximal member but the length of a distal member may be changed according to the femur length of a patient. All attachment means are tapered and held by threaded connection. It is not an integral stem and may be subject to loosening resulting in the displacement of the implant. It does not have porous coating to facilitate bone ingrowth.

U.S. patent application No. 2002/0138151 to Hubbard et al. discloses a cementless femoral hip stem component. The hip stem component includes an elongate stem, a proximal body, and a collar disposed on the proximal body and extending outward therefrom in a sideways direction to form a ledge. The proximal body defines at least a majority of a frustoconical shape. The ledge formed by the collar includes a tapered undersurface, beneath which extends the proximal body. The tapered undersurface of the ledge and the proximal body extend in different directions and thereby cooperatively define a double-flared contact surface configured to enable subsidable engagement of said double-flared contact surface with the femur at two different rates of subsidence within the femur. An abrupt, male corner is formed by the stem and the proximal body and is sufficiently abrupt to provide enhanced bone ingrowth stimulation. The prosthetic hip replacement system uses different porosity coatings at various locations of the stem and adjusts the location and angle of the neck element to minimize the stresses and maintain a natural biomechanics, which is clearly for human use. No disclosure is contained by the patent application concerning a canine femur stem.

There remains a need in the art for interchangeable canine femoral stems selected from a set of sizes permitting use of cemented or cementless procedures based on the situations during surgery. The implanted canine femoral stem must be usable immediately after surgery and develop long term permanent bond between the implant and the underlying bone structure meeting the needs of a dog. The implanted device must function satisfactorily throughout the lifetime of the dog without damage or deterioration.

SUMMARY OF THE INVENTION

Our present invention provides a canine femoral stem system, which provides multiple sizes of femoral stems attachable by cemented or cementless procedures matching interchangeably with a common-sized femoral head. The femoral stem and femoral head are selected by a surgeon depending upon the size of the dog and its bone condition. For example, if a bone defect is observed during surgery, the surgeon may choose to enlarge the size of the bone canal using a next size bone-reaming tool so as to accommodate a canine femoral stem of the next size. The plurality of cementless fixation and cement fixation femoral stems are provided to the surgeon at different sizes, having nominal diameters of 4 mm to 12 mm at 1 mm intervals (i.e., 4, 5, 6, 7, 8, 9, 10, 11 and 12 mm). The neck portion of the femoral stems attach with a common sized 17 mm femoral head by taper locking fit. Therefore, femoral stems of different sizes may be interchangeably used with common acetabular cup hardware providing reliable hip replacement even when the surgical situations may be problematic.

Each of the femoral stems is provided with a porous coating of sintered beads in the tapered proximal portion mating with controlled interference to fit in a femoral canal prepared by sequential broaching and a combination of tapered reamers and broaches provided. The surgeon may choose a canine femoral stem meeting the size of a dog and ream out the femoral canal. Each of the cementless biologic fixation (BFX) stems fit in the corresponding reamed canal with a controlled interference fit, providing intimate contact with the porous coating sintered on the canine femoral stem providing initial stability and encouraging bone ingrowth resulting in long term stability of the hip joint. If the bone structure does not permit use of the BFX option, the surgeon may select a cementation fixation system (CFX) femoral stem with similar size. The CFX canine femoral stem fits without interference within the reamed femoral canal interchangeably due to its design. In the cemented CFX canine femoral stem case, the initial stability is provided by the rapid cure of methyl methacralate cement or other cements.

The tapered distal end fits into the tapered lower region of the reamed femoral canal providing distal stability. The region of the stem in between the proximal and distal region is free from contacting the reamed femoral canal.

The canine femoral stem is fixed in the femoral canal with metaphyseal and diaphyseal sections. The Canine Femoral Stem System is especially suited for cemented or cementless hip replacement procedures wherein the acetabular and femoral components are press fit into their respective bones with or without cement. The canine femoral stem system affords initial stability and provides appropriate porosity for bone ingrowth, thereby providing long-term stability. The initial stability of the femoral stem in the cementless system is provided by 1) a taper fit into the bone canal at the distal end; 2) a tight fit frictional contact between the proximal end porous coating on the femoral stem; and 3) lack of fight contact between the bone canal and the intermediate region of the femoral stem. In the cemented system, features are identical except that a porous coating is not required. Long-term stability relies on bone ingrowth in the porous coating in the proximal end in the cementless system, while it is provided by cement hardening around the entire stem in the cemented system.

Typically a bone canal is reamed to install the femoral stem and corresponding acetabular cup. If the fit is improper, a different sized unit may be selected from the kit of femoral stems and acetabular cups to create a tight fit providing initial stability. However, if the bone canal for the femoral stem is too large to accomplish a tight fit, a cemented version is chosen to complete the implant operation. Since the parts are interchangeable, they mate together properly and attach to a 17 mm femoral head. This common sized femoral head mates correctly with acetabular cups fitted using cemented or cementless procedures.

The cementless fixation unit comprises a wrought cobalt chrome stem (alternately composed of Titanium 6Al-4V alloy) coated with 250 μm (±50 μm) diameter cobalt chrome beads, which are layered and then sintered circumferential to 45% of the proximal outer surface of the stem. The proximal portion of the canine femoral stem is tapered. The distal portion is directly anchored into the bone canal using a taper fit. Advantageously, the porous coating technology improves the potential for long-term success of the femoral component through bone ingrowth fixation. Initial stability is provided through friction between the sintered porous coating and the bone canal as well as the taper fit provided at the distal end of the canine femoral stem. Long-term stability is provided by bone ingrowth into the sintered porous coating.

The cement fixation unit comprises a cast cobalt chrome stem with a proximal tapering section having rounded corners and pockets for cement. The distal portion is tapered for better stress distribution to the cement. As a result, the implant has excellent initial stability, and can be reliably used immediately after surgery. Long-term stability is provided upon hardening of the cement.

The femoral stem incorporates several primary features, which address initial and long-term stability, and restoration of the hip biomechanics:

1. a sufficient number of stem sizes to provide a designed press fit for cementless implant procedures;
2. availability of compatible cemented femoral stems if the reamed bone canal is too large;
3. a stem design which allows mating with a femoral canal prepared by a sequential broaching method or a combination of tapered reamers and broaches;
4. a proximal section which is designed to fill and form a tight fit in the femoral canal;
5. a proximal section which has a porous surface completely circumferentially around stem;
6. a proximal section which has a porous surface created by sintering spherical beads of selected diameter to provide porosity sufficient for proximal bone ingrowth or for cement fixation;
7. a proximal geometry which has a lateral relief assisting in its insertion and avoidance of interference with the greater trochanter;
8. a distal conical-taper section of the canine femoral stem in both cemented or cementless systems designed to provide stability through contact with the distal taper canal of the bone;
9. a neck section which permanently and integrally connects to the proximal section of the stem and provides the ability to attach a femoral head of selected diameter and design through means of a locking taper;
10. a neck taper allowing for use of a 17 mm femoral head which is compatible with a cemented or cementless canine acetabular cup of a hip replacement system;
11. the designed use of a common femoral head between cemented and cementless systems that allows interchangeability between systems, so that the femur can be press fitted with a cementless or cemented femoral stem depending on the clinical situation observed at the time of surgery;
    a) the acetabulum can be addressed in the same manner allowing for stabilizing the implants with either cement or by press fit depending on the patient's quality of bone;
    b) any combination can be coupled by the same size of femoral head (i.e. cemented stem with press fit cup; press fit stem with cemented cup; press fit stem with press fit cup; and cemented stem with cemented cup);
12. a cementless system that has the option to be cemented, and provides initial stability through a mechanism wherein the cement hardens into the beads, instead of a mechanism that creates an interference fit with the bone.

The canine femoral stem can be constructed in a series of sizes, suitable for use with the anatomical canine acetablum sizes present in most canines. The canine femoral stem sizes range from 4 mm to 12 mm in 1 mm diameter increments.

BRIEF DESCRIPTION OF DRAWINGS

The invention will be more fully understood and further advantages will become apparent when reference is had to the following detailed description and the accompanying drawings, in which.

DESCRIPTION OF THE PREFERRED EMBODIMENTS

The present invention provides a femoral stem for canine hip replacements. The femoral stem comes in a range of sizes of 20 mm, 22 mm, 24 mm, 26 mm, 28 mm, 30 mm and 32 mm with a common femoral head of 17 mm. The surgeon may choose the size of femoral stem based on the bone size of the dog. If for any reason, the canal reamed is not according to the size requirements of the femoral stem, such as presence of bone defects, the next size may be chosen by selecting the next reamer and broach size, creating a hip implant that matches the femoral head and femoral prosthesis. The surgeon may choose the cementless biologic fixation system (BFX) or cemented fixation system (CFX) depending on the clinical situations during surgery. Thus the canine femoral stem system provides a variety of sizes of femoral stems that matches precisely with a 17 mm femoral head providing reliable hip replacement procedures.

In osteoarthritis and other related diseases of the hip, the effects on daily living can be debilitating resulting in the need to replace the joint with artificial implants. There are two methods for fixing these artificial hips to the bone:
1. cement fixation: both the acetabular component and the femoral component are cemented into their respective bones; and
2. cementless (press fit) fixation: both the acetabular and femoral components are press fit into their respective bones (without cement) in attempts for long-term fixation through biological ingrowth (bone and/or soft tissue attaching to the implants).

In cementless fixation, the method of providing a surface for bone and soft tissue to attach is by creating a surface of beads, which are tightly packed and attached by thermally sintering them to the body of the implant. Two types of materials have been clinically used during procedures involving cementless fixation:
1. Cobalt Chrome (ASTM F-75) with sintered cobalt chrome beads; and
2. Titanium (ASTM F-136) with sintered CP titanium beads.

The sintering of beads to the outer surface of the femoral stem component provides an irregular surface for interference (mechanical locking to the bone preparation) and porosity to provide for long-term stability through bone ingrowth and/or soft tissue attachment into the pores created by the layering of these small beads (a pocket is created on the surface which may require 3-4 layers of beads to fill.) There are many femoral stem designs in the human orthopedic field. In the veterinary field there are very few. The stem geometry can be divided into three distinct areas:
1. metaphyseal (proximal) section;
2. diaphyseal (distal) section; and
3. neck.

These areas address stability and fixation of the stem in the femoral canal (metaphyseal and diaphyseal sections) and provide the method for attaching a femoral head in the correct position for re-establishing the biomechanics of the hip. The success of a cementless design depends on its ability to offer initial stability, and secondarily provide appropriate porosity for bone ingrowth, thereby providing long-term stability. These cementless stems have used several different types of porous surfaces to provide bone the opportunity to mechanically attach. Such surfaces include plasma spray, layers of sintered beads and 3-D porous materials, which can be attached to the outer surface of the stem. The primary goal is to establish initial stability through the basic geometry of the stem that provides controlled interference with the reamed femoral bone canal. Based on clinical and research results, it has been established that this initial stability must provide for less than 150 μm of motion to allow the bone an opportunity to grow into the pores of the outer surface of the femoral stem. Motion exceeding this threshold during the initial stability phase of the procedure has shown to result in fibrous tissue ingrowth in the porous outer surface. When there is only fibrous tissue and no bone, or minimal bone ingrowth, loosening of the canine femoral stem can result. This scenario can require revision surgery to reestablish the implants.

The canine femoral stem system embodies a new and improved design and process attributes that addresses the issues of initial stability. In addition, a porous coating technology providing controlled interference is employed to improve the potential for long-term success of the femoral component through bone ingrowth fixation. This objective is achieved through implant geometry and bone preparation. The design of this cementless stem incorporates a cast cobalt chrome stem coated with 250 μm (±50 μm) diameter cobalt chromium beads, which are layered and then sintered to the outer surface of the stem. Alternatively a Titanium 6Al-4V alloy stem coated with 250 μm (±50 μm) diameter chemically pure titanium beads (CP Ti), which are sintered in layers to the outer surface of the stem can be used. The cast cobalt or titanium stem design incorporates several primary features, which address initial stability and long term bone ingrowth.

The canine femoral stem system will be more fully understood and further advantages will become apparent when reference is had to the accompanying drawings.

Figure 1:
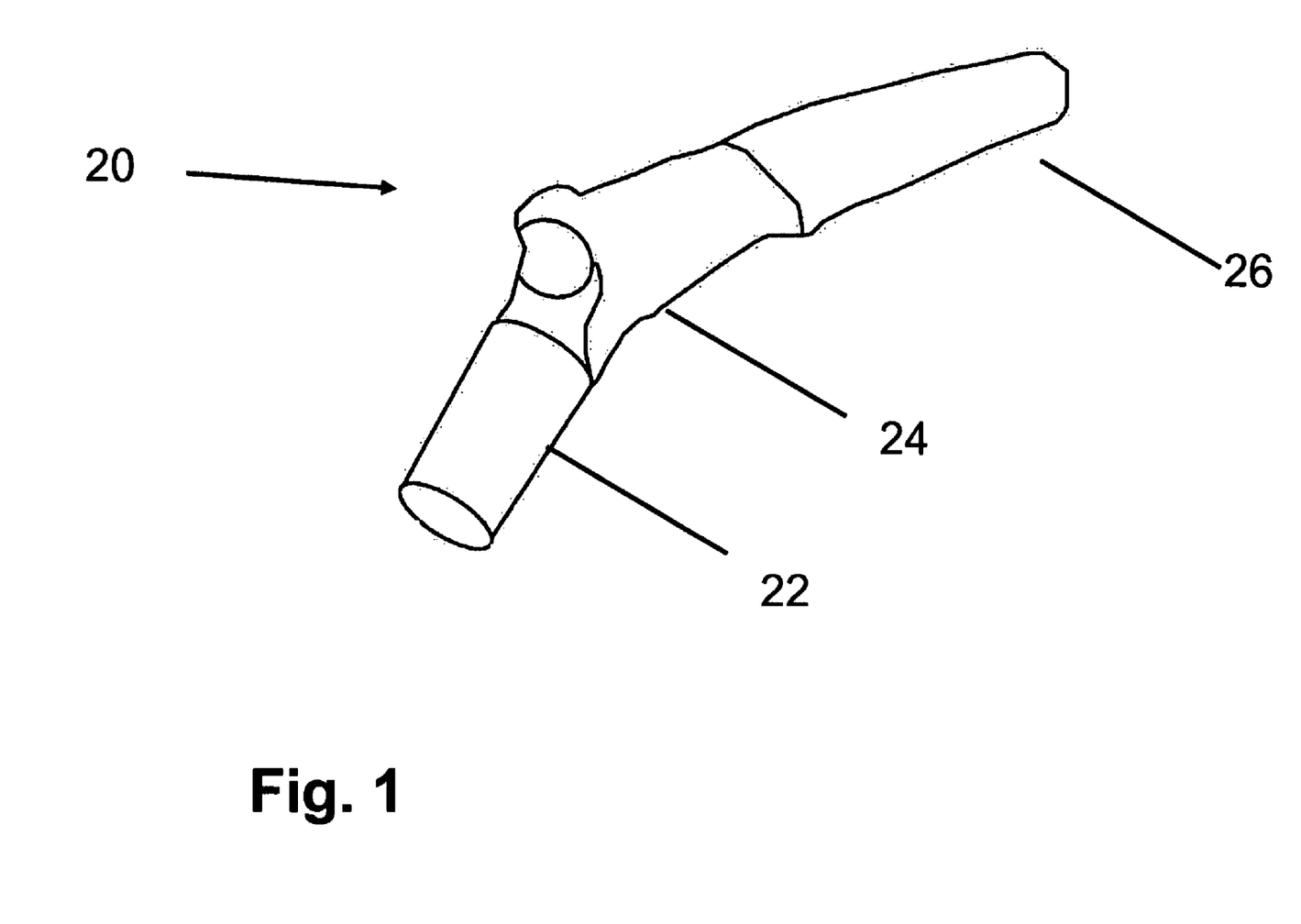
FIG. 1 contains a sketch depicting a computer model of the canine femoral stem in an assembled condition.

FIG. 1 contains a sketch depicting a computer model of the smallest canine femoral stem (20) in an assembled condition. The stem has a tapered neck 22 to accept a femoral head. It has a tapered distal end 26 with the proximal end 24 permanently attached as a one piece unit to the neck portion which carries a taper for accepting the femoral head.

Figures 2A, 2B:
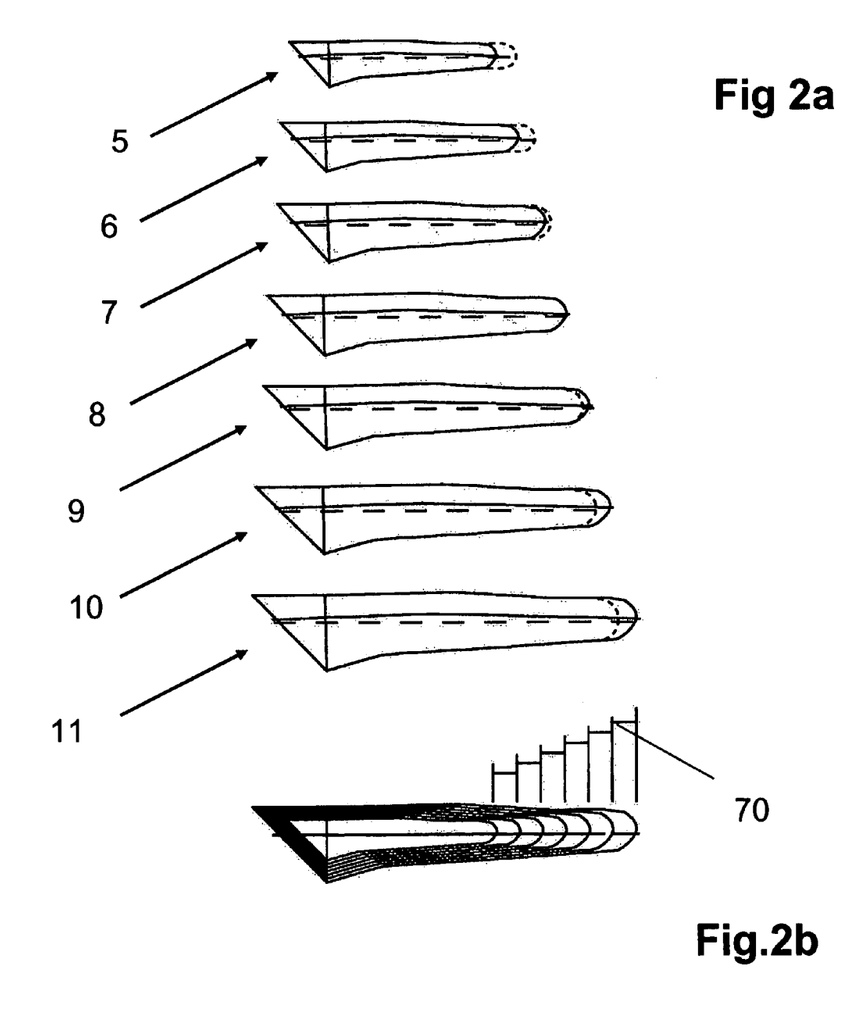
FIG. 2a contains a series of side views depicting a family of canine femoral stems of different sizes provided to a surgeon.
FIG. 2b illustrates the proportionate relationship between the femoral stems of different sizes.

FIG. 2a contains a series of side views depicting a family of canine femoral stems of different sizes provided to a surgeon and iLlustrates the proportionate relationship there between. The different sized stems 5, 6, 7, 8, 9, 10 and 11 are shown. The centerline for each femoral stem is shown as a dotted line and the overall center of the tapered stem is shown as a solid line. It is preferable to reduce the overall length of the larger size stems (9, 10 and 11) as indicated by the dotted lines. Correspondingly, the length of the smaller size (5, 6 and 7) canine femoral stems may be increased as indicated by the dotted lines for optimum fit. FIG. 2b shows the overall comparison of the proportional stern sizes of the different sized femoral stems. The difference in length 70 between one femoral stem and the next femoral stem is 6.29 mm.

Figures 3A, 3B:
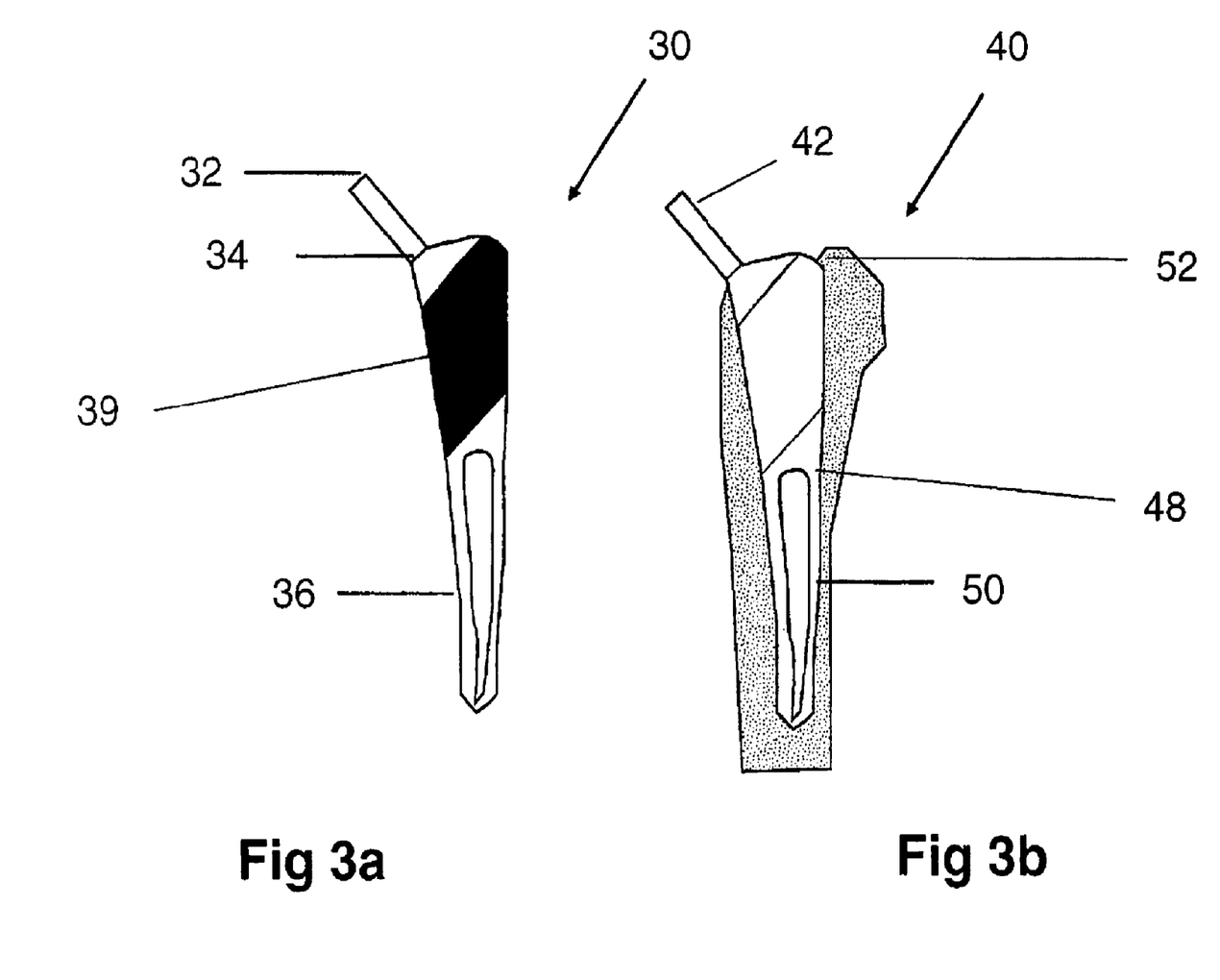
FIG. 3a illustrates basic features of the cementless BFX stem system.
FIG. 3b illustrates the relative positioning of the canine BFX femoral stem system within a reamed bone canal.

FIG. 3a and Fig 3b illustrates basic features of the cementless biologic fixation ("BFX") hip system. In cobalt chrome cast canine femoral stem, 250 μm cobalt chromium beads are sintered all around the tapered portion below the neck 32 of the BFX femoral stem 30 as indicated at 39. The distal portion of the stem 36 has a slight curvature as indicated. The dimensions in the coated tapered proximal section 34 of the canine femoral stem 30 is precisely maintained to assure reliable interference fit. Figure 3b shows the relative positioning of the canine BFX temoral stem 40 within a reamed bone canal (shown as the un-dotted portion of the bone). The sintered beads are in close interference contact with the reamed hone canal in the proximal portion 52 of the BFX stem 40. The initial stability of the implant is provided by friction resulting from interference of the tapered proximal portion 52 of the canine femoral stem just below the neck and the upper regions of a reamed femoral canal. This close contact between the bone and the porous coated region leads to bone ingrowth. The distal portion of the stem is indicated by 52. The curvature of the stem essentially presses against the lower region of the bone canal providing stabilizing effect. A medial portion 48 of the stem 40 positioned between the proximal 52 and distal portions 50 of the stem is free from contact with the reamed femoral canal. When the canine femoral stem is implanted, a lateral relief is maintained. The stem neck 42 angle is maintained at 135 degrees, This design is symmetrical for left or right side use. between the proximal 44 and distal portions 46 of the stem is free from contact with the reamed femoral canal 60. When the canine femoral stem is implanted, a lateral relief 47 is maintained. The stem neck 42 angle is maintained at 135 degrees. This design is symmetrical for left or right side use.

Figure 4:
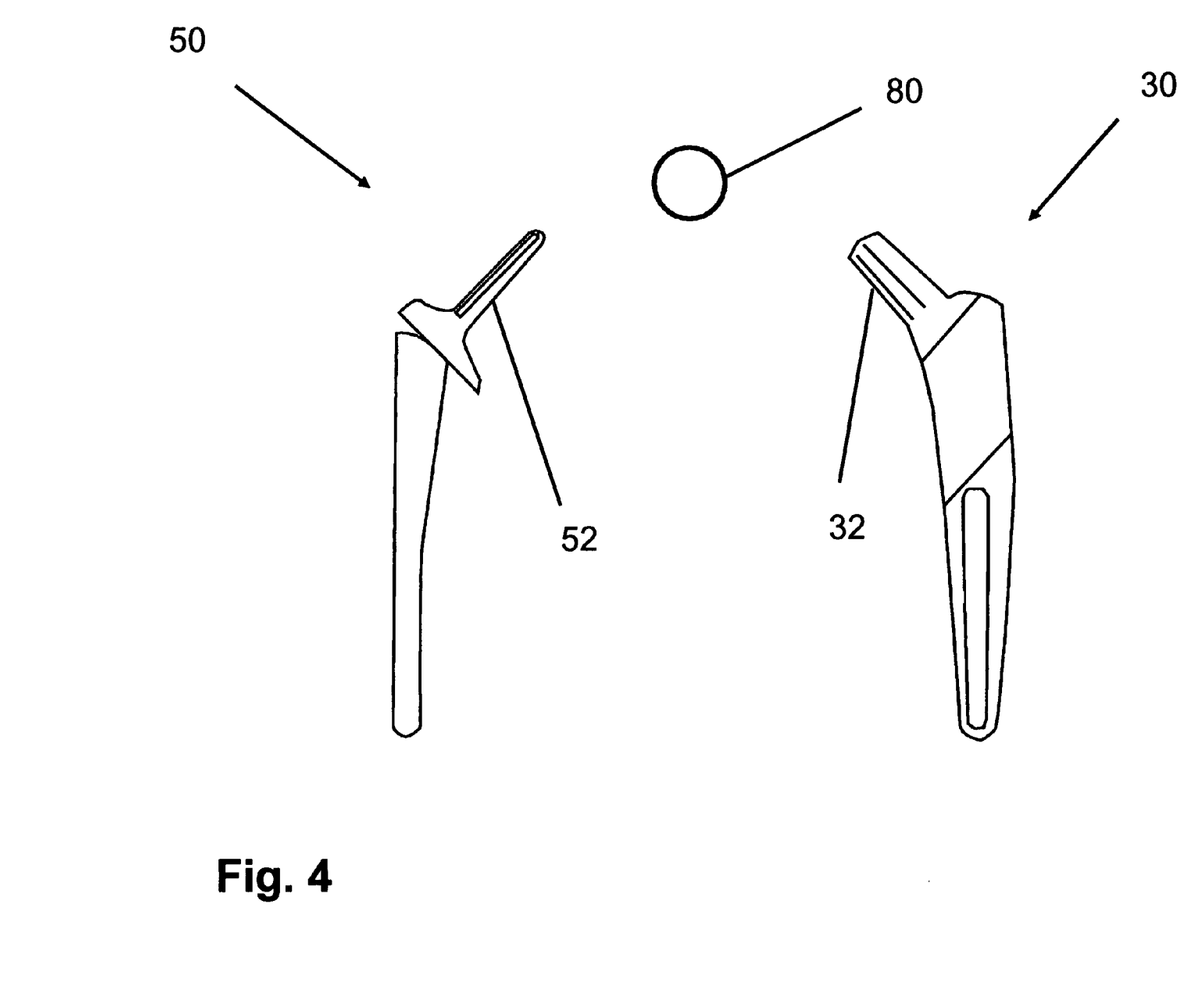
FIG. 4 illustrates the correlation between BFX and CFX system components, which permits utilization of a One Hip System using a common femoral head.

FIG. 4 illustrates the correlation between BFX and CFX system components, which permits utilization of a One Hip System wherein the neck of the BFX system 32 and the neck of the CFX system 52 mate with the same size of femoral head 80 which is 17 mm, providing an interchangeable system. The right side of the illustration shows the femoral stem 30 of BFX system wherein the canine femoral system is attached by controlled interference. The left side of the figure shows the corresponding femoral stem 50 of the cemented CFX system.

Figure 5:
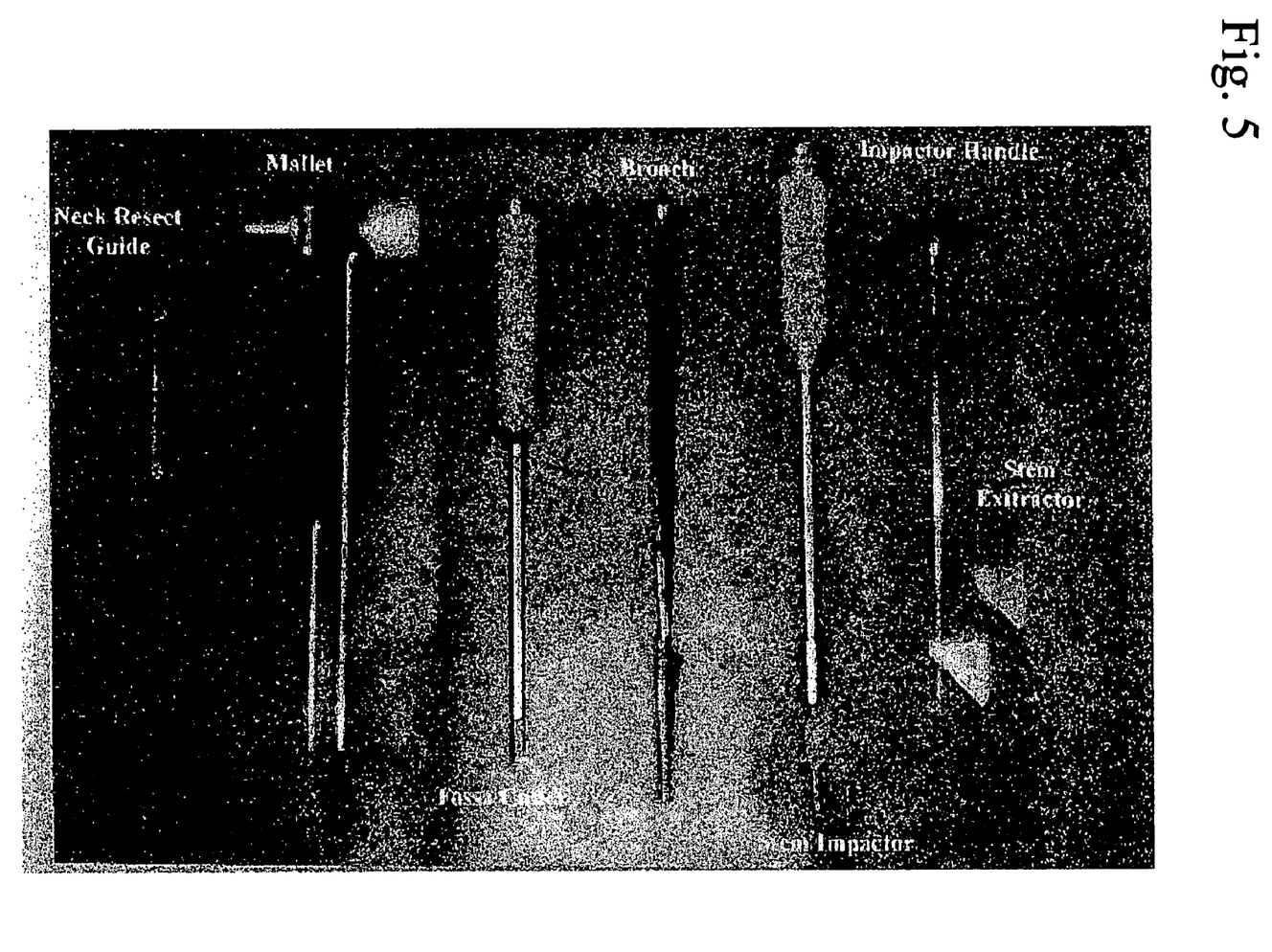
FIG. 5 depicts instruments required to prepare the bone for both the cup and stem in the BFX Canine Hip System.

FIG. 5 depicts instruments required to prepare the bone for both the cup and stem in the BFX Canine Hip System. These are a series of reamers and broaches and create a femoral bone cane canal that has a size appropriate with selected size of the canine femoral stem so as to create controlled interference fit.

The canine femoral stem system thus provides differently sized stems suitable for cementless biologic fixation (BFX) or cemented fixation (CFX) providing initial after surgery stability and long term stability having a combination of features set forth below:

1. Initial and long term stability of the Canine Femoral Stem accomplished by a taper fit of the canine femoral stem in the bone canal at the distal end and a frictional fit at the proximal end between porous bead coating and the bone canal in both cementless and cemented system;
2. Use of metallurgically bonded 250 μm±50 μm diameter cobalt chromium beads at the proximal end of a wrought cobalt chromium alloy femoral stem in the cementless BFX system with pore size sufficient to create bone ingrowth;
3. Availability of a sufficient number of stem sizes to provide a designed press fit for cementless implant procedures and availability of compatible cemented femoral stems if the reamed bone canal is too large;
4. A stem design, which allows mating with a femoral canal prepared by a sequential broaching or a combination of tapered reamers and broaches with a proximal section which is designed to fill and form tight fit in the femoral canal and distal end forming a taper fit with the intermediate section free from any tight contact with the bone canal; and
5. A neck section, which permanently and integrally connects to the proximal section of the stem and provides the ability to attach a femoral head of selected diameter and design compatible interchangeably with both the cementless and cemented system through a means of a locking taper.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A canine femoral stem system, comprising:
   a. a plurality of cementless fixation femoral stems (designed to be implanted by cementless procedure) having differing distal diameters and a plurality of cement fixation femoral stems (designed to be implanted by cement procedure) having differing distal diameters, where for each said cementless fixation femoral stem there is included a cement fixation femoral stem of similar size;
   b. one femoral head having a diameter of 17 mm, said cementless fixation and cement fixation stems being appointed for selection by a surgeon to interchangeably mate with said femoral head;
   c. each of said cementless fixation and cement fixation stems having a neck portion, a tapered proximal portion and a tapered distal portion, said tapered proximal portion being adapted to be implanted within an upper region of a reamed and/or broached femoral canal;
   d. said plurality of cementless fixation and cement fixation stems having a diverging taper proximally and symmetrical about the stem centerline in one plane providing for left or right femoral applications, and the angle of the neck portion being coincident with the stem centerline in one plane in order to prevent anteversion;
   e. the neck portions of said cementless fixation and cement fixation stems being adapted to interchangeably be attached to said femoral head to achieve a taper locking fit;
   f. the tapered proximal portions accounting for about 45% of the total stem surface area;
   g. the tapered distal portions include a curvature adapted to press against a lower region of said femoral canal providing a stabilizing effect upon insertion into said reamed and/or broached femoral canal, pressing against said lower region of said reamed and/or broached femoral canal, thereby providing distal stability;
   h. a medial region of each stem positioned between the proximal and distal portions being adapted to be free from contact with said femoral canal;
   i. said cementless fixation femoral stems comprising a layering of beads to encourage bone ingrowth, said beads being applied in an irregular (not smooth) manner, forming a porous coating, and being attached to the surface of said cementless femoral stems by thermal sintering; and
   j. said cement fixation femoral stems, absent of a porous coating, comprising pockets for cement.

2. A canine femoral stem system as recited by claim 1, wherein said plurality of cementless fixation and cement fixation stems have nominal diameters of 4, 5,6,7,8,9, 10,11 and 12 mm.

3. A canine femoral stem system as recited by claim 1, wherein said cementless fixation stems use a cast canine femoral stem of cobalt chromium alloy having sintered 250±50 μm diameter cobalt chromium beads.

4. A canine femoral stem system as recited by claim 1, wherein said cementless fixation stems use a cast or wrought canine femoral stem of titanium 6Al-4V alloy having sintered 250±50 μm diameter chemically pure titanium beads.

5. A canine femoral stem system as recited by claim 1, wherein said distal portion of said cementless fixation and cement fixation femoral stems include a curvature adapted to press against said lower region of said reamed and/or broached femoral canal enhancing said distal stabilizing effect.

* * * * *